United States Patent
Bristow

(10) Patent No.: US 9,815,760 B2
(45) Date of Patent: Nov. 14, 2017

(54) PROCESS FOR THE CO-PRODUCTION OF ACETIC ACID AND DIMETHYL ETHER

(71) Applicant: BP CHEMICALS LIMITED, Middlesex (GB)

(72) Inventor: Timothy Crispin Bristow, East Yorkshire (GB)

(73) Assignee: BP CHEMICALS LIMITED, Middlesex (GB)

( * ) Notice: Subject to any disclaimer, the term of this patent is extended or adjusted under 35 U.S.C. 154(b) by 0 days.

(21) Appl. No.: 15/311,925

(22) PCT Filed: Jun. 12, 2015

(86) PCT No.: PCT/EP2015/063157
§ 371 (c)(1),
(2) Date: Nov. 17, 2016

(87) PCT Pub. No.: WO2015/193188
PCT Pub. Date: Dec. 23, 2015

(65) Prior Publication Data
US 2017/0121264 A1   May 4, 2017

(30) Foreign Application Priority Data

Jun. 20, 2014  (EP) .................................... 14173357

(51) Int. Cl.
| | |
|---|---|
| *C07C 51/09* | (2006.01) |
| *C07C 41/09* | (2006.01) |
| *C07C 41/16* | (2006.01) |
| *C07C 67/37* | (2006.01) |
| *B01D 3/14* | (2006.01) |
| *B01D 3/32* | (2006.01) |
| *B01D 3/42* | (2006.01) |
| *C07C 41/42* | (2006.01) |

(52) U.S. Cl.
CPC .............. *C07C 51/09* (2013.01); *B01D 3/143* (2013.01); *B01D 3/322* (2013.01); *B01D 3/4205* (2013.01); *C07C 41/09* (2013.01); *C07C 41/16* (2013.01); *C07C 41/42* (2013.01); *C07C 67/37* (2013.01)

(58) Field of Classification Search
None
See application file for complete search history.

(56) References Cited

U.S. PATENT DOCUMENTS 7,465,822 B2    12/2008   Cheung et al.

FOREIGN PATENT DOCUMENTS

| WO | WO 2008/132438 A1 | 11/2008 |
| WO | WO 2008/132468 A1 | 11/2008 |
| WO | WO 2011/027105 A1 | 3/2011 |
| WO | WO 2013/124404 A1 | 8/2013 |
| WO | WO 2013/124423 A1 | 8/2013 |

*Primary Examiner* — Yate K Cutliff
(74) *Attorney, Agent, or Firm* — Nixon & Vanderhye P.C.

(57) ABSTRACT

Catalytic dehydration-hydrolysis process for the co-production of acetic acid and dimethyl ether from a mixture of methanol and methyl acetate and water in which the amount of water fed to the process is controlled by the steps of dehydrating a methanol feed to provide a crude product containing dimethyl ether, unconverted methanol and water, recovering therefrom a stream containing dimethyl ether, water and methanol and a water stream and separating dimethyl ether from the dimethyl-ether containing stream to produce a methanol stream containing methanol and water. At least part of the methanol stream and methyl acetate is supplied to the dehydration-hydrolysis process.

18 Claims, 1 Drawing Sheet

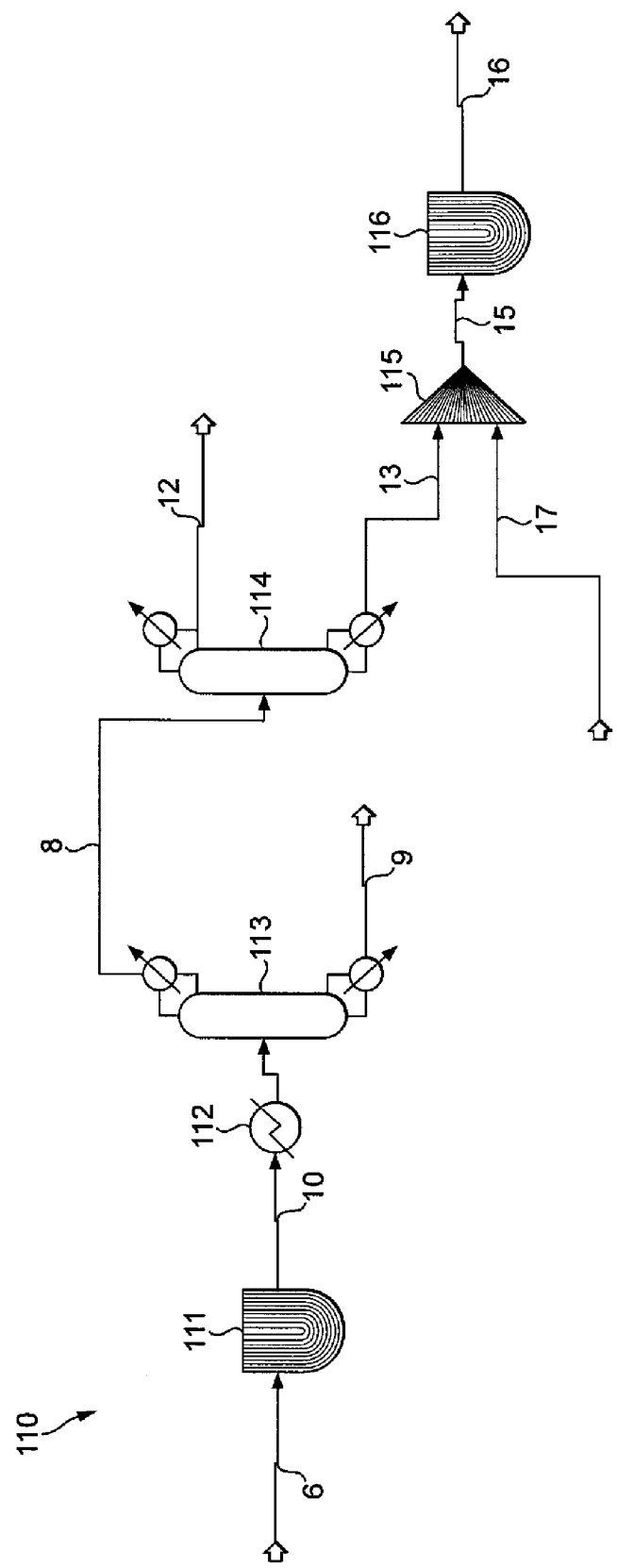

PROCESS FOR THE CO-PRODUCTION OF ACETIC ACID AND DIMETHYL ETHER

This application is the U.S. national phase of International Application No. PCT/EP2015/063157 filed Jun. 12, 2015 which designated the U.S. and claims priority to European Patent Application No. 14173357.6 filed Jun. 20, 2014, the entire contents of each of which are hereby incorporated by reference.

The present invention relates to a process for the co-production of acetic acid and dimethyl ether from methanol, methyl acetate and water and, in particular to a process for the co-production of acetic acid and dimethyl ether from methanol, methyl acetate and water in which the amount of water fed to the process is controlled.

BACKGROUND OF THE INVENTION

Processes for the co-production of acetic acid and dimethyl ether may be carried out by the catalytic dehydration and hydrolysis of mixtures of methanol and methyl acetate. Such co-production processes are known from, for example WO 2011/027105, WO 2013/124404 and WO 2013/124423.

WO 2011/027105 describes a process for the production of acetic acid and dimethyl ether by contacting methanol and methyl acetate with a catalyst composition at a temperature in the range 140 to 250° C. wherein the catalyst composition contains a zeolite having a 2-dimensional channel system comprising at least one channel which has a 10-membered ring.

WO 2013/124404 describes a process for the co-production of acetic acid and dimethyl ether from a mixture of methanol and methyl acetate by contacting the mixture at a temperature from 200 to 260° C. with a catalyst composition comprising a zeolite possessing a 2-dimensional channel system comprising at least one channel having a 10-membered ring and a silica:alumina molar ratio of at least 22.

WO 2013/124423 describes a process for the production of acetic acid and dimethyl ether by contacting a mixture of methanol and methyl acetate with a zeolite catalyst wherein the zeolite has a 2-dimensional channel system comprising at least one channel having a 10-membered ring and having at least 5% of its cation exchange capacity occupied by one or more alkali metal cations.

In such dehydration-hydrolysis processes methanol is dehydrated to dimethyl ether and methyl acetate is hydrolysed to acetic acid. The reactions can be represented by:

2 methanol ⇌ dimethyl ether+water

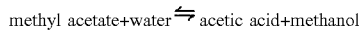
methyl acetate+water ⇌ acetic acid+methanol

These reactions are equilibrium limited. The hydrolysis reaction consumes water and produces methanol and the dehydration reaction consumes methanol and produces water.

It has now been found that in the presence of solid acid catalysts, such as zeolites, the dehydration reaction is relatively slow and since water is consumed more quickly by the hydrolysis reaction, it is typically necessary to provide water to the system to maintain a steady-state concentration of water in the reaction. Water may be added to the dehydration-hydrolysis process as a component of process streams such as water-containing feed and recycle streams to the process.

In general, methanol obtained by commercial synthesis processes contains water and may also contain some dimethyl ether. The amount of water in the methanol product can vary depending upon such factors as the composition of the feed to the process and the process conditions, and in particular the amount of carbon dioxide employed in the methanol synthesis process.

Methyl acetate may be produced by processes for carbonylating ethers, such as the carbonylation of dimethyl ether with carbon monoxide, as described, for example in U.S. Pat. No. 7,465,822, WO 2008/132438 and WO 2008/132468. Although the principal reaction of dimethyl ether with carbon monoxide does not itself produce water, it has now been found that low levels of water can be produced via side-reactions taking place in the carbonylation process.

Thus the amount of water present in feeds, particularly in methanol feeds, to dehydration-hydrolysis processes may be sub-optimal for maintaining or optimising the operation of such processes. Furthermore, if such processes are operated as continuous processes, recycling of water-containing streams to the process can cause or contribute to fluctuations in the water concentration within the process. Water losses due to, for example leaks in the process can also create fluctuations in water concentration within the system. Such fluctuations need to be managed to maintain effective process operation.

SUMMARY OF THE INVENTION

Thus, there remains a need for a process for the co-production of acetic acid and dimethyl ether from methanol and methyl acetate in which the amount of water in the process can be controlled.

Accordingly, the present invention provides a process for the co-production of acetic acid and dimethyl ether by the dehydration-hydrolysis of a mixture of methanol and methyl acetate carried out at a temperature of 100 to 350° C. at atmospheric or greater pressure in the presence of at least one solid acid catalyst and water to generate a reaction product comprising dimethyl ether and acetic acid in which process the amount of water to the dehydration-hydrolysis is controlled by:

dehydrating a methanol feed comprising methanol and water to generate a crude dehydration product comprising dimethyl ether, unconverted methanol and water;

recovering from the crude dehydration product i) a dimethyl ether stream comprising dimethyl ether, water and methanol and ii) a water stream;

separating dimethyl ether from the dimethyl ether stream to produce a methanol stream comprising methanol and water; and supplying to the dehydration-hydrolysis reaction the methanol stream or a part thereof, methyl acetate and optionally one or more recycle streams comprising one or more of methanol, methyl acetate and water.

Advantageously, in the process of the present invention, the amount of water supplied to a dehydration-hydrolysis process may be controlled by utilising a separate dehydration step upstream of the combined dehydration-hydrolysis process. In this manner, water can be removed from the system, as part of the dehydration step, in varying and controlled amounts dependent upon the water requirements of the dehydration-hydrolysis process to maintain effective operation.

Furthermore, the present invention provides for enhanced production of dimethyl ether which may be utilised subsequently as a feedstock in other chemical processes, and in particular as a feedstock to carbonylation processes for the production of methyl acetate.

In a preferred embodiment of the present invention, recovery of the water stream from a crude dehydration product may be carried out by distillation methods, for example by fractional distillation, in one or more distillation columns. Preferably, distillation is carried out in a single distillation column, preferably equipped with a reboiler.

In some or all embodiments of the present invention, recovery of the water stream from a crude dehydration product is carried out by fractional distillation, in a distillation column equipped with a reboiler, wherein (i) the dimethyl ether stream is recovered as a heads product from the column; and (ii) the water stream is recovered as a base stream from the column.

Preferably, in these embodiments, the amount of water recovered as a base stream from the distillation column is controlled by adjusting one or both of the reflux ratio and reboiler duty to the distillation column.

In some or all embodiments of the present invention, the water stream is recovered from a crude dehydration product which comprises up to 45 mol %, such as 20 to 45 mol % dimethyl ether, 10 to 60 mol % methanol and >0 to 60 mol %, for example 20 to 60 mol % water by distillation in a distillation column equipped with a reboiler. Suitably, the distillation column has 15 theoretical stages or thereabouts and is operated at a pressure of 5 barg to 30 barg (500 to 3000 kPa), a heads temperature of 120 to 165° C. and a reflux ratio of 0.05 to 1. Preferably, in these embodiments the recovered water stream is essentially pure water. A preferred boil-up ratio is 0.01 to 5.

In some or all embodiments of the present invention, the water stream is recovered from a crude dehydration product which comprises up to 45 mol %, such as 20 to 45 mol % dimethyl ether, 10 to 60 mol % methanol and >0 to 50 mol %, for example 20 to 45 mol % water by distillation in a distillation column equipped with a reboiler, the distillation column containing 15 theoretical stages or thereabouts and operated at a pressure of 5 barg to 30 barg (500 to 3000 kPa), a heads temperature of 120 to 165° C. and a reflux ratio of 0.05 to 1. Preferably, in these embodiments the recovered water stream is essentially pure water. A preferred boil-up ratio is 0.01 to 5.

In some or all embodiments of the present invention, dimethyl ether may be separated from a recovered dimethyl ether stream by distillation methods, for example by fractional distillation, in one or more distillation columns.

In a preferred embodiment, dimethyl ether is separated from the dimethyl ether stream in a distillation column wherein (i) dimethyl ether is recovered as a heads product from the column; and (ii) a methanol stream is recovered as a base stream from the column.

In this preferred embodiment a methyl acetate-rich stream is introduced as an additional feed into the distillation column and methyl acetate is recovered as a component of the methanol stream recovered from the column. At least a portion of the methanol stream recovered from the column and comprising methyl acetate is supplied to the dehydration-hydrolysis process.

In some or all embodiments of the present invention, at least a portion of methyl acetate for supply to the dehydration-hydrolysis process is recovered from a process for the carbonylation of dimethyl ether with carbon monoxide in the presence of a carbonylation catalyst, preferably a zeolite catalyst and optionally hydrogen.

In some or all embodiments of the present invention, the process further comprises recovering from the dehydration-hydrolysis reaction product, an acetic acid-rich stream and a dimethyl ether-rich stream, for example by distillation methods, such as by fractional distillation, in one or more distillation columns.

The present invention further provides an integrated process for the co-production of acetic acid and dimethyl ether by the dehydration-hydrolysis of methanol and methyl acetate carried out at a temperature of 100 to 350° C. and at atmospheric or greater pressure in the presence of at least one solid acid catalyst and water to generate a reaction product comprising dimethyl ether and acetic acid in which process the amount of water to the dehydration-hydrolysis is controlled by:

converting a gaseous mixture of carbon monoxide, hydrogen and optionally carbon dioxide in the presence of a methanol synthesis catalyst to produce a methanol feed comprising methanol and water;

dehydrating the methanol feed comprising methanol and water to generate a crude dehydration product comprising dimethyl ether, unconverted methanol and water;

recovering from the crude dehydration product i) a dimethyl ether stream comprising dimethyl ether, water and methanol and ii) a water stream;

separating dimethyl ether from the dimethyl ether stream to produce a methanol stream comprising methanol and water; and supplying to the dehydration-hydrolysis reaction the methanol stream or a part thereof, methyl acetate and optionally one or more recycle streams comprising one or more of methanol, methyl acetate and water.

In preferred embodiment, the conversion of the gaseous mixture of carbon monoxide and hydrogen in the presence of a methanol synthesis catalyst to produce the methanol feed comprising methanol and water is carried out with added carbon dioxide.

In a preferred embodiment, the gaseous mixture of carbon monoxide and hydrogen and optional carbon dioxide is recovered from a process for the carbonylation of dimethyl ether with carbon monoxide in the presence of a carbonylation catalyst, preferably a zeolite catalyst, and hydrogen and optionally carbon dioxide to produce a crude carbonylation reaction product comprising methyl acetate and carbon monoxide, hydrogen and optional carbon dioxide.

BRIEF DESCRIPTION OF THE DRAWINGS

The invention is further described with reference to the accompanying drawing, in which:

The FIGURE is a schematic diagram illustrating an embodiment of the present invention for the co-production of acetic acid and dimethyl ether.

DETAILED DESCRIPTION OF THE INVENTION

In the process of the present invention a methanol feed comprising methanol and water is dehydrated to generate a crude dehydration product comprising dimethyl ether, unconverted methanol and water.

Preferably, the methanol feed comprises mainly methanol, such as in an amount of 50 mol % or more, for example 50 to 99 mol %, preferably 80 mol % or more.

Suitably, the methanol feed contains water in an amount >0 mol % to 35 mol %, for example 5 to 20 mol %.

The methanol feed may also contain small amounts of dimethyl ether, for example in an amount of 10 mol % or less.

In one or all embodiments of the present invention, the methanol feed comprises 50 to 99 mol % methanol, such as 80 to 90 mol % methanol, >0 to 35 mol % water, such as 5 to 20 mol % water and 0 to 10 mol % dimethyl ether.

Methanol feeds for use in the process of the present invention include those synthesised by the catalytic conversion of a gaseous mixture of carbon monoxide and hydrogen and optionally carbon dioxide according to the overall equation CO+2H$_2$ ⇌ CH$_3$OH. The reaction proceeds in accordance with the following equations:

  (I)

  (II)

Typically, a gaseous mixture of carbon monoxide and hydrogen and optionally carbon dioxide is a synthesis gas, such as those generated commercially, for example by steam reforming or partial oxidation processes. In general, synthesis gas contains carbon dioxide in amounts of 15 mol % or less, such as 2 to 10 mol %. Methanol feeds so-produced comprise mainly methanol together with lesser amounts of water and they may also contain some dimethyl ether.

Methanol synthesis is usually carried out in the presence of a catalyst. A number of catalysts active for methanol synthesis are known in the art and are commercially available. Typically, catalysts for methanol synthesis comprise copper as an active catalytic component and may contain one or more additional metals such as zinc, magnesium and aluminium. Examples of methanol synthesis catalysts include but are not limited to catalysts comprising zinc oxide and alumina as the support with copper as the active catalytic component.

A methanol synthesis catalyst may be employed in a fixed bed, for example in the shape of pipes or tubes, where the mixture of carbon monoxide and hydrogen and optionally carbon dioxide is passed over or through the catalyst.

In general, methanol synthesis is carried out at a temperature of from 210° C. to 300° C. and at a total pressure of from 25 to 150 barg (2500 to 15,000 kPa).

Usefully, a methanol synthesis process may be integrated with the co-production process of the present invention. Thus, the present invention further provides an integrated process for the co-production of acetic acid and dimethyl ether by the dehydration-hydrolysis of a mixture of methanol and methyl acetate carried out at a temperature of 100 to 350° C. and at atmospheric or greater pressure in the presence of at least one solid acid catalyst and water to generate a reaction product comprising dimethyl ether and acetic acid in which process the amount of water to the dehydration-hydrolysis is controlled by:

converting a gaseous mixture of carbon monoxide, hydrogen and optionally carbon dioxide in the presence of a methanol synthesis catalyst to produce a methanol feed comprising methanol and water;

dehydrating the methanol feed comprising methanol and water to generate a crude dehydration product comprising dimethyl ether, unreacted methanol and water;

recovering from the crude dehydration product i) a dimethyl ether stream comprising dimethyl ether, water and methanol and ii) a water stream;

separating dimethyl ether from the dimethyl stream to produce a methanol stream comprising methanol and water; and supplying to the dehydration-hydrolysis reaction the methanol stream or a part thereof, methyl acetate and optionally one or more recycle streams comprising one or more of methanol, methyl acetate and water.

In some or all embodiments, the conversion of the gaseous mixture of carbon monoxide and hydrogen and optional carbon dioxide is carried out in the presence of a methanol synthesis catalyst comprising copper as an active catalytic component to produce a methanol feed comprising methanol and water and optionally dimethyl ether.

The methanol feed or part thereof comprising methanol and water generated in the methanol synthesis may be supplied directly or indirectly to the dehydration step for dehydration therein to generate a crude dehydration product comprising dimethyl ether, unreacted methanol and water. Unreacted gases present in the methanol feed may be separated therefrom, for example by separation in a flash drum prior to dehydration of the methanol feed.

A methanol feed comprising methanol and water may be dehydrated as a vapour or a liquid, preferably as a vapour. If the methanol feed contains liquid phase components, the liquid components may, if desired, be volatilised, for example using a pre-heater.

Dehydration of the methanol feed may be carried out in the presence of any suitable catalyst which is effective to dehydrate methanol to generate dimethyl ether and water. Useful catalysts include solid acid catalysts including aluminas such as gamma-alumina and fluorinated alumina, acidic zirconias, aluminium phosphate, silica-alumina supported tungsten oxides and solid Brønsted acid catalysts such as heteropolyacids and salts thereof and aluminosilicate zeolites.

The term "heteropolyacid" as used herein and throughout this specification is meant to include the free acids. Heteropolyacids for use herein may be used either as free acids or as partial salts. Typically, the heteropolyacid, or the anionic component of its corresponding salt comprises 2 to 18 oxygen-linked polyvalent metal atoms, which are called peripheral atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I-VIII in the Periodic Table of elements. These include, for example cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well-known anions are named after the original researchers in this field and are known, for example as Keggin, Wells-Dawson and Anderson-Evans-Perloff structures.

Heteropolyacids usually have a high molecular weight, for example in the range from 700-8500 and include dimeric complexes. They have a relatively high solubility in polar solvents such as water or other oxygenated solvents, especially if they are free acids and in the case of several salts, and their solubility can be controlled by choosing the appropriate counter-ions. Specific examples of heteropolyacids that may be usefully utilised in the present invention include the free acids such as silicotungstic acids, phosphotungstic acids and 12-tungstophosphoric acid (H$_3$[PW$_{12}$ $O_{40}$].$xH_2O$); 12-molybdophosphoric acid ($H_3$[$PMo_{12}O_{40}$].$xH_2O$); 12-tungstosilicic acid ($H_4$[$SiW_{12}O_{40}$].$xH_2O$); 12-molybdosilicic acid ($H_4$[$SiMo_{12}O_{40}$].$xH_2O0$ and ammonium salts of heteropolyacids, such as ammonium salts of a phosphotungstic acid or a silicotungstic acid.

Particularly useful dehydration catalysts include zeolites having a 2-dimensional or 3 dimensional channel system and at least one channel of which has a 10-membered ring. Specific non-limiting examples of such zeolites include zeolites of framework type FER (typified by ferrierite and ZSM-35), MFI (typified by ZSM-5), MFS (typified by ZSM-57), HEU (for example clinoptilolite) and NES (typified by NU-87).

The three-letter codes such as 'FER' refer to the framework structure type of the zeolites using the nomenclature proposed by the International Zeolite Association. Information about structure codes and zeolites is available in the Atlas of Zeolite Framework Types, C. H. Baerlocher, L. B. Mccusker and D. H. Olson, 6th Revised Edition, Elsevier, Amsterdam, 2007 and is also available on the website of the International Zeolite Association at www.iza-online.org.

Zeolites utilised in the dehydration of the methanol feed may be employed in an exchanged form. Exchanged forms of zeolites can be prepared by techniques such as ion-exchange and impregnation. These techniques are well-known in the art and typically involve the exchange of the hydrogen or ammonium cations of a zeolite with metal cations. For example, in the present invention, the zeolite may be in an exchanged form with one or more alkali metal cations for example sodium, lithium, potassium and cesium. Suitable exchanged form zeolites include ferrierite and ZSM-35 exchanged with one or more of sodium, lithium, potassium and cesium.

A zeolite may be used in the form of a composite with any suitable binder material. Examples of suitable binder materials include inorganic oxides, such as silicas, aluminas, alumina-silicates, magnesium silicates, magnesium aluminium silicates, titanias and zirconias. Preferred binder materials include aluminas, alumina-silicates and silicas. Suitably, a binder material may be present in the composite in an amount of from 10 to 90 wt % based on the total weight of zeolite and binder material.

In a preferred embodiment, dehydration of the methanol feed is conducted as a heterogeneous process either as a liquid phase or vapour phase process.

Suitably, dehydration is conducted at temperatures of about 100° C. to 350° C. or higher such as about 100° C. to 450° C. depending on the specific type of reactor employed.

Preferably, liquid phase processes are conducted at temperatures of about 140° C. to 210° C.

Suitably, vapour phase processes are conducted at temperatures of about 100° C. to 450° C., preferably about 150° C. to 300° C.

Dehydration of the methanol feed may be conducted at atmospheric pressure or at elevated pressure.

In one or more embodiments of the present invention, dehydration is carried out in the liquid phase at a total pressure which is sufficient to maintain dimethyl ether product in solution, for example a total pressure of 40 barg or more, preferably at a pressure of 40 to 100 barg and suitably at a temperature of about 140° C. to 210° C. In such cases dehydration may be carried out at a liquid hourly space velocity (LHSV) is in the range 0.2 to 20 $h^{-1}$.

In one or more embodiments of the present invention dehydration is carried out in the vapour phase at operating pressures of atmospheric to 30 barg (atmospheric to 3000 kPa), for example 10 to 20 barg (1000 to 2000 kPa) and suitably at a temperature of about 100° C. to 450° C., preferably about 150° C. to 300° C. In such cases dehydration may be carried out at a gas hourly space velocity (GHSV) in the range 500 to 40,000 $h^{-1}$.

In one or more embodiments of the present invention, dehydration is carried out in the presence of at least one catalyst selected from gamma-aluminas and zeolites, suitably zeolites of framework type FER or MFI and under operating conditions which are maintained such that the dehydration is conducted in the vapour phase, suitably at a temperature of about 150° C. to 300° C. and at a total pressure of atmospheric to 30 barg (atmospheric to 3000 kPa). In such cases dehydration may be carried out at a gas hourly space velocity (GHSV) in the range 500 to 40,000 $h^{-1}$.

Dehydration of the methanol feed comprising methanol and water generates a crude dehydration product comprising dimethyl ether, water and unreacted methanol. In general as water is generated in the reaction, the crude dehydration product contains a greater amount of water than the feed methanol. Desirably, a crude dehydration product comprises 45 mol % or less, for example about 20 to 45 mol % dimethyl ether, about 20 to 45 mol % water and about 10 to 60 mol % methanol.

Dehydration of methanol feeds comprising 50 to 99 mol %, such as 80 to 90 mol % methanol, >0 to 35 mol %, such as 5 to 20 mol % water and 0 to 10 mol % dimethyl ether can typically produce crude dehydration products which comprise 45 mol % or less, for example about 20 to 45 mol % dimethyl ether, about 20 to 45 mol % water and about 10 to 60 mol % methanol.

Recovery of dimethyl ether streams comprising dimethyl ether, water and methanol and water streams from a crude dehydration products can, in principle, be achieved by any conceivable method, however preference is given to distillation methods, for example by fractional distillation of the crude dehydration product.

A distillation method in which one or more columns, preferably one column may be employed to separate the crude dehydration product to recover i) a dimethyl ether stream and ii) a water stream. Desirably, if a single column is employed, it has at least 5, such as at least 10 theoretical stages, such as at least 15 theoretical stages. Since distillation zones may have differing efficiencies 15 theoretical stages may be equivalent to at least 25 actual stages with an efficiency of about 0.7 or at least 30 actual stages with an efficiency of about 0.5.

Suitably, a distillation column may be a tray or packed column.

Suitably, a distillation column is operated at elevated pressure, such as at a pressure of about 0.5 barg (50 kPa) or more, such as about 5 barg to 30 barg (500 to 3000 kPa), for example about 5 to 20 barg (500 to 2000 kPa).

At pressures of about 5 barg to 30 barg (500 to 3000 kPa), for example about 5 to 20 barg (500 to 2000 kPa), the heads temperature of the column may be about 120° C. to 180° C., for example about 120° C. to 165° C.

In a preferred embodiment, separation of the crude dehydration product to recover i) a dimethyl ether stream comprising dimethyl ether, water and methanol and ii) a water stream, suitably a stream consisting essentially of water, is carried out in a distillation column which has 15 theoretical stages or thereabouts and is operated at a pressure of about 5 barg to 30 barg (500 to 3000 kPa), for example about 5 to 20 barg (500 to 2000 kPa) and at a heads temperature of about 120° C. to 165° C.

A dimethyl ether stream comprising dimethyl ether, methanol and water is recovered from distillation of the crude dehydration product as a heads stream from the column. The exact composition of the heads stream will vary depending on the composition of the feed and the desired amount of water to be removed in the water stream from the column. The more water removed from the column, the richer the heads stream will become in dimethyl ether and methanol. In general, however distillation of the crude dehydration product results in a dimethyl ether stream which comprises mainly dimethyl ether together with smaller amounts of methanol and water. Desirably, a dimethyl ether stream comprises >0 to 60 mol %, such as 10 to 40 mol % methanol and >0 to 60 mol %, such as 5 to 45 mol %, for example 5 to 40 mol % water and dimethyl ether, for example 40 to 90 mol % dimethyl ether.

Typically, the dimethyl ether stream withdrawn from a distillation column as a heads stream is withdrawn as a vapour.

A water stream separated from the crude dehydration product by distillation is typically withdrawn from a distillation column as a base stream. Desirably, the water stream comprises essentially pure water, however it may suitably comprise 90 mol % or more water, preferably 95 mol % or more water, more preferably 95 to 99 mol % or more water.

The quantity of water exiting a distillation column in which the crude dehydration product is distilled can be adjusted dependent upon the amount of water desired to be fed to the dehydration-hydrolysis process. The amount of water to a dehydration-hydrolysis process can be determined by compositional analysis, for example by gas chromatography, of stream(s) supplied to the process. If the total amount of water to the dehydration-hydrolysis process is less than desired, the amount of water exiting the distillation column in the base stream may be decreased. Similarly, if the total amount of water to the dehydration-hydrolysis process is greater than desired, the amount of water exiting the column in the base stream may be increased.

Control of the amount of water exiting the distillation column in the base stream may be achieved by adjusting one or both of the reflux ratio and reboiler duty (boil-up ratio) to the column. Regulation of the reflux ratio and reboiler duty will also control the composition of the water stream exiting the column. A distillation column may be operated with a return of liquid reflux to the head of the column at a reflux to overhead ratio dependent upon such factors as the desired overhead stream composition. Increasing the reflux ratio increases the flow rate of water from the column and also increases the amount of methanol and dimethyl ether present in the water stream.

In preferred embodiments, recovery of the dimethyl ether and water streams from the crude dehydration product is carried out in a distillation column operated with a reflux ratio of 0.05 to 1. A preferred boil-up ratio is 0.01 to 5.

Preferably a distillation column is equipped with a reboiler at the base of the column. The reboiler may be of any suitable type for use with the distillation column, for example it may be of the shell and tube heat exchanger type, such as a thermo-syphon or kettle type reboiler. Steam may be used as the heat source in the reboiler. Increasing the reboiler duty to the column, typically by means of a temperature controller, decreases the flow rate of water removed from the column and also decreases the amount of methanol and dimethyl ether present in the water stream removed from the column.

Water streams recovered from distillation or otherwise may be utilised to generate steam, re-utilised in other processes and/or, if desired may be discarded from the process as a waste effluent.

Preferably, separation of dimethyl ether from dimethyl ether streams recovered from the crude dehydration product is implemented by distillation methods. Preference is given to a distillation method in which one or more distillation columns, preferably a single distillation column, is employed. Suitably, a single column may have at least 5, such as at least 15 theoretical stages, such as at least 20 theoretical stages, for example 20 to 40 theoretical stages.

A distillation column may be operated at elevated pressure, such as at a pressure of about 0.5 barg (50 kPa) or more, such as about 0.5 barg to 30 barg (50 to 3000 kPa), for example about 10 to 30 barg (1000 to 3000 kPa).

In one or more embodiments, dimethyl ether is separated from a dimethyl ether stream by distillation in a distillation column which has 20 theoretical stages or thereabouts and operated at a pressure of about 0.5 barg (50 kPa) or more, such as about 0.5 barg to 30 barg (50 to 3000 kPa), for example about 10 to 30 barg (1000 to 3000 kPa).

A dimethyl ether stream may be introduced into the column as vapour or as a liquid.

Preferably, dimethyl ether is separated from the dimethyl ether stream by distillation in a distillation column wherein
  (i) dimethyl ether is recovered as a heads product from the distillation column;
  (ii) a methanol stream comprising methanol and water is recovered as a base stream from the distillation column;

Typically, the majority of the dimethyl ether present in the dimethyl ether feed to the distillation column is removed as a heads product from the column. The heads product may be removed as a liquid or as a vapour, preferably as a vapour. Recovered dimethyl ether may be supplied to processes which require dimethyl ether as a starting material or in another function.

Suitably, a methanol stream removed from the distillation column comprises methanol and water and it may also comprise some dimethyl ether. In general, the methanol stream may have a dimethyl ether content of 3 mol % or less, for example 0 to 2 mol %.

Suitably, the distillation column is operated with a return of liquid reflux to the head of the column at a reflux to overhead ratio dependent upon such factors as the required overhead stream composition. A suitable reflux ratio may be in the range 1 to 10, for example 1.5 to 2.5. A suitable boil-up ratio may be 0.01 to 5.

In preferred embodiments of the present invention, one or more methyl acetate-rich streams may be introduced into the distillation column and methyl acetate is recovered from the column as a component of the methanol stream. Desirably, methyl acetate-rich feeds introduced into the distillation column comprise mainly methyl acetate, preferably in an amount of at least 50 mol %. A methyl acetate feed to the distillation column may be introduced into the column as a liquid or a vapour or a mixture thereof.

Methyl acetate for supply to the distillation column may be recovered from processes for the carbonylation of dimethyl ether with carbon monoxide in the presence of a carbonylation catalyst, preferably a zeolite catalyst such as mordenite and preferably in the presence of hydrogen. Such processes are known, for example from U.S. Pat. No. 7,465,822, WO 2008/132438 and WO 2008/132468.

Typically, methyl acetate streams recovered from such carbonylation processes comprise mainly methyl acetate and may also comprise additional components such as one or more of unreacted dimethyl ether, methanol and water. In general, a methyl acetate stream may comprise dimethyl ether in an amount of 50 mol % or less, for example of about 5 to 45 mol %. Typically, a methyl acetate stream might comprise 50 to 95 mol % methyl acetate and 5 to 45 mol % dimethyl ether.

Contaminants such as one or both of acetaldehyde and methyl formate may be generated via side-reactions occurring in methanol synthesis processes and/or methyl acetate production processes. Advantageously, such contaminants present in one or more feeds to the distillation column (for separating dimethyl ether from the dimethyl ether stream) may be conveniently removed therefrom as a sidedraw from the column. Suitably, a sidedraw stream is withdrawn from the distillation column at a point above the base of the column and at or above the introduction of the feeds) to the column. Preferably, the sidedraw stream is withdrawn from the distillation column as a liquid.

Recovery of contaminants as a sidedraw stream from the column can be enhanced by providing sufficient stripping capacity in the distillation column below the feed point(s) to the column. Suitably, the distillation column has at least 3 theoretical stages, for example 3 to 33 theoretical stages, below the feed point of the dimethyl ether feed to the column.

In preferred embodiments, for a distillation column having 20 to 40 theoretical stages, the methyl acetate feed point may be at stage 10 to 25 counted from the head, the dimethyl ether feed point may be at stage 5 to 25 from the head and a sidedraw stream may be withdrawn, preferably as a liquid, at stages 4 to 15 from the head and at or above the dimethyl ether and methyl acetate feed points to the column.

The methanol stream or a part thereof comprising methanol and water and optionally and preferably methyl acetate is supplied as feed to the dehydration-hydrolysis process. Desirably, the total amount of acetaldehyde and methyl formate contaminants in the methanol stream is 500 ppm or less, for example 250 ppm or less and preferably 100 ppm or less.

The methanol stream or a part thereof comprising methanol and water and optionally and preferably methyl acetate is contacted in the presence of at least one catalyst to generate a reaction product comprising acetic acid and dimethyl ether. The hydrolysis of methyl acetate to generate acetic acid and dehydration of methanol to form dimethyl ether can be represented by equations (1) and (2) respectively:

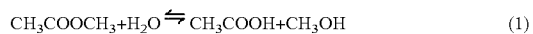

$$CH_3COOCH_3 + H_2O \rightleftharpoons CH_3COOH + CH_3OH \quad (1)$$

$$2CH_3OH \rightleftharpoons CH_3OCH_3 + H_2O \quad (2)$$

In addition to any methyl acetate supplied as a component of the methanol stream it is entirely feasible to supply additional methyl acetate, as one or more methyl acetate feeds, to the dehydration-hydrolysis reaction.

One or more solid acid catalysts may be utilised in the dehydration-hydrolysis reaction. One or more catalysts may be employed which are effective to catalyse both the hydrolysis and dehydration reactions. Alternatively, one or more catalysts effective for catalysing hydrolysis may be used in addition to or as an admixture with one or more catalysts effective for dehydration. Suitable dehydration catalysts include the above-mentioned solid acid catalysts for the dehydration of the methanol feed comprising methanol and water to generate the crude dehydration product. Zeolites known to be effective for the hydrolysis of methyl acetate to produce acetic acid include zeolite Y, zeolite A, zeolite X and mordenite. If desired, these zeolites can be usefully employed as a catalyst in the dehydration-hydrolysis reaction of the present invention.

If it is desired to employ two or more different catalysts, the catalysts may be utilised in the form of alternating catalyst beds or as one or more intimately mixed catalyst beds.

In preferred embodiments, a catalyst for the dehydration-hydrolysis reaction is selected from one or more zeolites of framework type, FER (for example ferrierite and ZSM-35) and MFI (for example ZSM-5). These zeolites may be employed in an exchanged form, suitably in an exchanged form with one or more alkali metal cations, such as sodium, lithium, potassium and cesium.

Preferably, a zeolite is used in the dehydration-hydrolysis reaction in composite form with a binder material. Examples of suitable binder materials include inorganic oxides, such as silicas, aluminas, alumina-silicates, magnesium silicates, magnesium aluminium silicates, titanias and zirconias. The relative proportions of zeolite and binder material may vary widely but suitably, the binder material may be present in a composite in an amount of 10% to 90% by weight of the composite.

Certain Brønsted acid catalysts including heteropolyacids and salts thereof and aluminosilicate zeolites have been found to be sensitive to some aldehyde compounds, particularly when utilised in hydrolysis processes for the production of acetic acid. Thus, where it is desired to utilise such catalysts in the present invention it is preferred that the methanol stream optionally comprising methyl acetate and any additional methyl acetate feeds to the dehydration-hydrolysis reaction comprise acetaldehyde in a total amount of 100 ppm or less.

To mitigate fluctuations or imbalances of water concentration in one or both of the methanol and methyl acetate feeds to the dehydration-hydrolysis reaction, the water concentration of feeds, including any recycles, to the process is determined, for example by gas chromatography, and if desired the total amount of water to the dehydration-hydrolysis reaction may be controlled by, as discussed above, utilising a methanol dehydration process in which a methanol feed comprising water is dehydrated to generate a crude dehydration product, which crude dehydration product is preferably distilled by fractional distillation in a distillation column equipped with a reboiler and the quantity of water removed is adjusted by regulating one or both of the reflux ratio and reboiler duty to the column to increase or decrease the amount of water recovered from distillation and hence from the process.

Suitably, water may be introduced into the dehydration-hydrolysis reaction in an amount of about 0.1 to 50 mol %, such as about 5 to 30 mol %, for example about 20 to 30 mol %, based on the total feed of methyl acetate, water and methanol to the reaction.

The molar ratio of methanol to methyl acetate supplied to the dehydration-hydrolysis may be any desired ratio, but suitably the molar ratio of methanol:methyl acetate is in the range 1:0.1 to 1:20, for example 1:0.2 to 1:10.

The dehydration-hydrolysis reaction may be carried out as a heterogeneous vapour phase process or as a liquid phase process. If it is desired to conduct the reaction as a vapour phase process, it is preferable to volatilise liquid feed(s), for example in a pre-heater prior to contact with the catalyst.

The dehydration-hydrolysis reaction is carried out at temperatures of about 100° C. to 350° C. and at atmospheric pressure or pressures greater than atmospheric.

In one or more embodiments, the dehydration-hydrolysis reaction is conducted as a vapour phase process at a temperature of about 150° C. to 350° C. and a pressure of atmospheric to 30 barg (atmospheric to 3000 kPa), for example 5 to 20 barg (500 kPa to 2000 kPa). Suitably, in such cases, the dehydration-hydrolysis reaction is carried out at a gas hourly space velocity (GHSV) in the range 500 to 40,000 $h^{-1}$.

In one or more embodiments dehydration-hydrolysis reactions conducted as liquid phase processes are carried out at temperatures of from about 140° C. to about 210° C. and at a pressure which is sufficient to maintain dimethyl ether product in solution, such as pressures of 40 barg (4000 kPa) or higher, for example 40 to 100 barg (4000 to 10,000 kPa). Suitably, in such cases, the dehydration-hydrolysis reaction is carried out at a liquid hourly space velocity (LHSV) in the range 0.2 to 20 $h^{-1}$.

The dehydration-hydrolysis reaction may be carried out using any suitable technique and apparatus, for example by reactive distillation. Reactive distillation techniques and apparatus therefor are well-known. The methanol stream comprising methanol and water and optionally methyl acetate, can be supplied to a conventional reactive distillation column, operated at, for example a pressure in the range atmospheric to 20 barg (atmospheric to 2000 kPa) and at a reaction temperature of about 100° C. to 350° C., to produce a crude reaction product comprising a mixture of acetic acid and dimethyl ether, which mixture is inherently separated within the reactive distillation column to recover a product stream rich in dimethyl ether, typically recovered as an overhead from the column, and a product stream rich in acetic acid which is typically recovered as a base stream from the column.

Alternatively, the dehydration-hydrolysis reaction may be carried out in a fixed bed reactor or a slurry bed reactor. Dimethyl ether has a low boiling point (−24° C.) and acetic acid has a high boiling point (118° C.). Thus, acetic acid and dimethyl ether may be recovered from the reaction product by conventional purification methods, such as by distillation in one or more conventional distillation columns. Suitable distillation columns include tray or packed columns. The temperatures and pressures employed in the columns can vary. Suitably, a distillation column may be operated at a pressure, for example of atmospheric to 20 barg (0 to 2000 kPa). Typically, a stream rich in dimethyl ether is recovered as an overhead from the distillation column, and a stream rich in acetic acid is recovered as a base stream from the column.

Acetic acid may be sold or may be used as a feedstock in a variety of chemical processes, such as the manufacture of vinyl acetate or ethyl acetate.

Dimethyl ether may be sold or used as a fuel or as a feedstock to carbonylation or other chemical processes.

The co-production process of the present invention may be operated as a continuous process or as a batch process, preferably operated as a continuous process.

The invention is now illustrated with reference to the following non-limiting Examples.

Example 1

This Example demonstrates a process for the co-production of acetic acid and dimethyl ether in which the amount of water fed to the process is controlled in accordance with the present invention. Reference is made to the FIGURE and Tables 1 and 2. The FIGURE illustrates schematically an integrated unit (110) for carrying out embodiments of the process of the present invention. A wet methanol stream (6) comprising methanol, water and dimethyl ether is introduced continuously, preferably as a vapour stream and a GHSV of 500 to 40,0001Y1 into reactor (111) containing a dehydration catalyst, suitably a solid acid catalyst, suitably a zeolite catalyst. Suitably, the reactor is maintained under conditions of 100 to 350° C., preferably 150 to 300° C. and a pressure of 10 to 20 barg. In the reactor, dehydration of the methanol takes place to produce a crude dehydration product (10) comprising dimethyl ether, water and unreacted methanol which is withdrawn from reactor (111), preferably passed to a heat exchanger (112) to cool the crude dehydration product to and is introduced into distillation column (113) equipped with a reboiler. Distillation column (113) has 15 theoretical stages with feed of the crude dehydration product to stage 10 (counted from the head of the column) and is operated at elevated pressure, preferably 5 to 30 barg (500 to 3000 kPa) and a heads temperature of 120 to 180° C. A water stream (9) comprising essentially water is removed as a base stream from the column (113). A dimethyl ether stream (8) comprising dimethyl ether, methanol and water is removed from the column (113) as a heads stream, condensed and a portion thereof is returned to the column at a reflux ratio of 0.05 to 1 and a boil-up ratio of 0.01 to 5. The dimethyl ether stream (8) is passed to distillation column (114) equipped with a reboiler. Distillation column (114) has 20 theoretical stages with the dimethyl ether feed point at stage 10 (counted from the head of the column) and is operated at elevated pressure, preferably 1 to 20 barg (100 to 2000 kPa), a reflux ratio of 1 to 4 and a boil-up ratio of 0.01 to 5. Dimethyl ether is withdrawn from the distillation column (114) as heads stream (12) and a methanol stream (13) comprising methanol and water is withdrawn as a base stream from the column. The methanol stream (13) and a methyl acetate stream (17) is mixed in mixer (115), for example a T-piece and the mixed stream (15) is supplied to dehydration-hydrolysis reactor (116), such as a fixed bed reactor wherein it is contacted with at least one solid acid catalyst, for example a heteropolyacid or zeolite catalyst at elevated pressure and a temperature of 100 to 350° C. to generate a reaction product comprising acetic acid and dimethyl ether, withdrawn from reactor (116) as product stream (16).

Utilising the procedure and apparatus of the type illustrated in the FIGURE, simulations were carried out using ASPEN software version 7.3. The stream compositions (in krnol/hr and mol %) for operation of distillation column (113) at a reflux ratio of 0.3 and a boil-up ratio of 0.025 and distillation column (114) at a reflux ratio of 2.2 and boil-up ratio of 0.19 are shown in Table 1 below and for operation of distillation column (113) at a reflux ratio of 0.15 and a boil-up ratio of 2.2 and distillation column (114) at a reflux ratio of 3.1 and boil-up ratio of 0.12 the results are shown in Table 2 below. In the Tables, the following abbreviations are used:

MeOH—methanol
AcOH—acetic acid
DME—dimethyl ether
MeOAc—methyl acetate

As can be seen from a comparison of the results in Table 1 and Table 2, adjusting the reflux ratio of distillation column (113) allows the quantity of water withdrawn as a base stream from the column to be controlled. In particular, increasing the reflux ratio from 0.15 to 0.3 in distillation column (113) increases the amount of water removed from the column as water stream (6) and decreases the amount of water fed to the dehydration-hydrolysis reactor (116).

TABLE 1

| mol flow | Stream 6 | | Stream 10 | | Stream 9 | | Stream 8 | | Stream 12 | | Stream 13 | | Stream 17 | | Stream 15 | | Stream 16 | |
|---|---|---|---|---|---|---|---|---|---|---|---|---|---|---|---|---|---|---|
| | | | | | | | | | mol % | | | | | | | | | |
| MeOH | 850.0 | 85.0 | 123.5 | 12.4 | 11.5 | 5.0 | 112.0 | 14.5 | 0.2 | 0.0 | 111.8 | 32.9 | 0.0 | 0.0 | 111.8 | 8.3 | 41.6 | 3.1 |
| AcOH | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 168.8 | 12.6 |
| Water | 80.0 | 8.0 | 443.2 | 44.3 | 215.2 | 94.2 | 228.0 | 29.6 | 0.0 | 0.0 | 228.0 | 67.0 | 0.0 | 0.0 | 228.0 | 17.0 | 178.7 | 13.3 |
| DME | 70.0 | 7.0 | 433.2 | 43.3 | 1.7 | 0.7 | 431.5 | 55.9 | 431.2 | 100.0 | 0.3 | 0.1 | 0.0 | 0.0 | 0.3 | 0.0 | 119.8 | 8.9 |
| MeOAc | 0.0 | 0.0 | 0.0 | 0.0 | 0.0 | 0.0 | 0.0 | 0.0 | 0.0 | 0.0 | 0.0 | 0.0 | 1000.0 | 100.0 | 1000.0 | 74.6 | 831.2 | 62.0 |

TABLE 2

| mol flow | Stream 6 | | Stream 10 | | Stream 9 | | Stream 8 | | Stream 12 | | Stream 13 | | Stream 17 | | Stream 15 | | Stream 16 | |
|---|---|---|---|---|---|---|---|---|---|---|---|---|---|---|---|---|---|---|
| | | | | | | | | | mol % | | | | | | | | | |
| MeOH | 850.0 | 85.0 | 123.5 | 12.4 | 0.0 | 0.0 | 123.5 | 13.0 | 0.2 | 0.0 | 123.3 | 23.8 | 0.0 | 0.0 | 123.3 | 8.1 | 60.1 | 4.0 |
| AcOH | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 214.1 | 14.1 |
| Water | 80.0 | 8.0 | 443.2 | 44.3 | 47.8 | 100.0 | 395.4 | 41.5 | 0.0 | 0.0 | 395.4 | 76.1 | 0.0 | 0.0 | 395.4 | 26.0 | 319.9 | 21.1 |
| DME | 70.0 | 7.0 | 433.2 | 43.3 | 0.0 | 0.0 | 433.2 | 45.5 | 432.7 | 100.0 | 0.5 | 0.1 | 0.0 | 0.0 | 0.5 | 0.0 | 139.2 | 9.2 |
| MeOAc | 0.0 | 0.0 | 0.0 | 0.0 | 0.0 | 0.0 | 0.0 | 0.0 | 0.0 | 0.0 | 0.0 | 0.0 | 1000.0 | 100.0 | 1000.0 | 65.8 | 785.9 | 51.7 |

The invention claimed is:

1. A process for the co-production of acetic acid and dimethyl ether by dehydration-hydrolysis of a mixture of methanol and methyl acetate carried out at a temperature of 100 to 350° C. and at atmospheric or greater pressure in the presence of at least one solid acid catalyst and water to generate a reaction product comprising dimethyl ether and acetic acid in which process the amount of water to the dehydration-hydrolysis is controlled by:
dehydrating a methanol feed comprising methanol and water to generate a crude dehydration product comprising dimethyl ether, unconverted methanol and water
recovering from the crude dehydration product i) a dimethyl ether stream comprising dimethyl ether, water and methanol and ii) a water stream;
separating dimethyl ether from the dimethyl ether stream to produce a methanol stream comprising methanol and water; and
supplying to the dehydration-hydrolysis reaction the methanol stream or a part thereof, methyl acetate and optionally one or more recycle streams comprising one or more of methanol, methyl acetate and water.

2. A process according to claim 1 wherein recovery of the water stream from the crude dehydration product is carried out by fractional distillation in a single distillation column equipped with a reboiler to recover the dimethyl ether stream as a heads product from the column and the water stream as a base stream from the column.

3. A process according to claim 2 wherein the amount of water recovered as a base stream from the distillation column is controlled by adjusting one or both of reflux ratio and reboiler duty (boil-up ratio) to the column.

4. A process according to claim 2 wherein distillation is carried out at a reflux ratio of from 0.05 to 1.

5. A process according to claim 4 wherein the distillation is carried out at a boil-up ratio of 0.01 to 5.

6. A process according to claim 2 wherein distillation is carried out at a pressure of 5 to 30 barg (500 to 3000 kPa) and at a heads temperature of 120 to 180° C.

7. A process according to claim 1 wherein the water stream recovered from the crude dehydration product comprises 90 mol % or more water.

8. A process according to claim 7 wherein the dimethyl ether stream recovered as a heads product from the column comprises >0 to 60 mol % methanol, 5 to 45 mol % water and the balance dimethyl ether.

9. A process according to claim 1 wherein the methanol feed to dehydration comprises water in an amount of from >0 to 35 mol %.

10. A process according to claim 9 wherein the methanol feed to dehydration comprises 50 to 99 mol % methanol, >0 to 35 mol % water and 0 to 10 mol % dimethyl ether.

11. A process according to claim 1 wherein the methanol feed to dehydration is derived from conversion of a gaseous mixture of carbon monoxide, hydrogen and optionally carbon dioxide in the presence of a methanol synthesis catalyst.

12. A process according to claim 1 wherein the dehydration is conducted as a vapour phase process at a pressure of atmospheric to 30 barg (atmospheric to 3000 kPa) and at a temperature of 100° C. to 450° C.

13. A process according to claim 1 wherein the dehydration is conducted as a liquid phase process at a pressure of 40 to 100 barg (4000 to 10000 kPa) and at a temperature of 140° C. to 210° C.

14. A process according to claim 1 wherein the dehydration of the methanol feed is carried out in the presence of a solid acid catalyst which solid acid catalyst is a zeolite selected from zeolites having a 2-dimensional or 3-dimensional channel system and at least one channel of which has a 10-membered ring.

15. A process according to claim 1 wherein dimethyl ether is separated from the dimethyl ether stream comprising dimethyl ether, water and methanol to produce a methanol stream comprising methanol and water by distillation in a single distillation column.

16. A process according to claim 1 wherein water is introduced to the dehydration-hydrolysis reaction in an amount of 0.1 to 50 mol % based on the total feed of methyl acetate, water and methanol.

17. A process according to claim 1 wherein the solid acid catalyst for the dehydration-hydrolysis reaction is selected from one or more heteropolyacids and salts thereof and zeolites.

18. A process according to claim 1 wherein the process is operated as a continuous process.

* * * * *